(12) United States Patent
Watanabe et al.

(10) Patent No.: US 7,575,551 B2
(45) Date of Patent: Aug. 18, 2009

(54) BIOLOGICAL SIGNAL MONITOR DEVICE

(75) Inventors: Yoshinobu Watanabe, Kadoma (JP);
Hisashi Hagiwara, Kadoma (JP);
Yoshinao Tannaka, Kadoma (JP);
Takao Suzuki, Kadoma (JP)

(73) Assignee: Panasonic Corporation, Osaka (JP)

( * ) Notice: Subject to any disclaimer, the term of this patent is extended or adjusted under 35 U.S.C. 154(b) by 109 days.

(21) Appl. No.: 10/569,661

(22) PCT Filed: Aug. 30, 2004

(86) PCT No.: PCT/JP2004/012891

§ 371 (c)(1),
(2), (4) Date: Feb. 24, 2006

(87) PCT Pub. No.: WO2005/020821

PCT Pub. Date: Mar. 10, 2005

(65) Prior Publication Data

US 2007/0032725 A1    Feb. 8, 2007

(30) Foreign Application Priority Data

Sep. 1, 2003    (JP) .............................. 2003-309196

(51) Int. Cl.
*A61B 8/00* (2006.01)
(52) U.S. Cl. ........................................ 600/443; 128/916
(58) Field of Classification Search ................. 600/437, 600/443, 450; 128/916
See application file for complete search history.

(56) References Cited

U.S. PATENT DOCUMENTS 5,289,820 A * 3/1994 Beach et al. ................. 600/443

(Continued)

FOREIGN PATENT DOCUMENTS

JP    2889568    2/1999

(Continued)

OTHER PUBLICATIONS

Hiroshi Kanai et al., "Imagining of Elasticity Distribution in Arterial Wall by Transcutaneous Ultrasound and Electronic Staining.", Rinsho Byori, 2003, vol. 51, No. 8, pp. 805-812.

(Continued)

*Primary Examiner*—Eric F Winakur
*Assistant Examiner*—Michael T Rozanski
(74) *Attorney, Agent, or Firm*—Hamre, Schumann, Mueller & Larson, P.C.

(57) ABSTRACT

There is provided an excellent biological signal monitor device that allows a living tissue moving in accordance with a body motion or a vibration to be observed as if it were standing still. A reverse correction processing unit (114) subjects a B-mode image to reverse correction based on a movement amount of the living tissue detected by a movement amount detection unit (113), and outputs the B-mode image corresponding to the living tissue moving in accordance with a body motion as quasi-still image information. An arithmetic processing unit (115) subjects the quasi-still image information from the reverse correction processing unit (114) to arithmetic processing such as averaging and filter processing, so as to remove a random noise component. As a result, it is possible to display, for example, a contour portion of a blood vessel wall as the living tissue clearly.

18 Claims, 14 Drawing Sheets

U.S. PATENT DOCUMENTS

| | | | |
|---|---|---|---|
| 5,840,028 | A | 11/1998 | Chubachi et al. |
| 5,885,218 | A * | 3/1999 | Teo et al. .................... 600/443 |
| 6,132,373 | A | 10/2000 | Ito et al. |
| 6,139,497 | A | 10/2000 | Amemiya et al. |
| 6,224,557 | B1 | 5/2001 | Ziel et al. |
| 6,270,459 | B1 | 8/2001 | Konofagou et al. |
| 6,352,507 | B1 * | 3/2002 | Torp et al. .................... 600/438 |
| 6,464,643 | B1 | 10/2002 | Brock-Fisher |
| 2004/0260180 | A1 | 12/2004 | Kanai et al. |

FOREIGN PATENT DOCUMENTS

| | | |
|---|---|---|
| JP | 2000-229078 | 8/2000 |
| JP | 2000-271117 | 10/2000 |
| JP | 2003-126090 | 5/2003 |
| WO | WO 03/015635 A1 | 2/2003 |

OTHER PUBLICATIONS

H. Hasegawa et al., "Automatic Detection of Lumen-Intima Boundary of Posterior Wall of Carotid Artery.", Technical Report if IEICE, 2003, vol. 103, No. 158, pp. 5-10.

Kanai, H. et al. "Real-Time Measurements of Local Myocardium Motion and Arterial Wall Thickening", IEEE Transactions on Ultrasonics, Ferroelectrics and Frequency Control, vol. 46, No. 5, Sep. 199, pp. 1229-1241.

* cited by examiner

BIOLOGICAL SIGNAL MONITOR DEVICE

TECHNICAL FIELD

The present invention relates to a medical ultrasonic diagnostic apparatus. In particular, the invention relates to a biological signal monitor device that noninvasively and successively performs the measurement of an amount of movement of a body tissue in accordance with a body motion such as a heartbeat, the extraction of a contour, the measurement of a blood vessel diameter, the measurement of an Intima Media Thickness (hereinafter, referred to as an "IMT value") of a blood vessel wall (carotid artery), and the like, so as to use the measurement results for a diagnosis of arteriosclerosis or the like.

BACKGROUND ART

Conventionally, as a method for noninvasively and successively performing the determination of the boundary of a living tissue or a blood vessel wall, the measurement of a value of a blood vessel inner diameter, the measurement of an IMT value, or the like by using an ultrasonic diagnostic apparatus, it has been known to use a luminance signal of image data for measurement, to obtain an IMT value (see, for example, JP 2000-271117 A (page 3, FIG. 1) and Japanese Patent No. 2889568 B (page 5, FIG. 8)), or the like based on a standard structure of a living tissue or a blood vessel wall. However, there has been no discussion in the prior art for displaying a body tissue moving in accordance with a body motion, as if it were standing still, or a prior art for using the quasi-still information for structural analysis of the body tissue, and thus no prior art document is referred to.

In the above-mentioned prior art, in order to extract the boundary of a living tissue, it is necessary to obtain a still image in which a random noise component is suppressed to a certain level or lower. However, in the case where the living tissue as a target moves in accordance with a body motion or the like, when a general noise filter for images is used to remove a random noise component, a living tissue component as a target of image analysis also is influenced by the noise filter. As a result, a contour is displayed with degraded sharpness and the like, making it difficult to perform precise structural analysis of a living tissue.

In particular, in an actual medical diagnosis of a carotid artery, there is the following problem. That is, since luminance information of image data is used for structural analysis of a target blood vessel wall, there is little difference in luminance between a random noise component and a signal corresponding to a tunica intima tissue in a living body having low tunica intima luminance or the like. Accordingly, it is impossible to perform precise structural analysis of a living tissue stably and easily.

DISCLOSURE OF INVENTION

The present invention was made in view of the forgoing problems, and it is an object of the present invention to provide an excellent biological signal monitor device that can provide a live image yet allows a living tissue moving in accordance with a body motion to be observed as if it were standing still by bringing the movement of the living tissue to a quasi-standstill or performing reverse correction with a movement amount of the living tissue, can remove a random noise component existing in a living tissue portion moving in accordance with a body motion by using a general noise filter for images, and can provide a clear B-mode image in which the random noise component existing in the living tissue portion moving in accordance with a body motion is reduced by subjecting echo data from which the noise has been removed to reverse conversion into a state where the living tissue moves in accordance with a body motion.

In order to achieve the above-mentioned object, a first biological signal monitor device according to the present invention includes: ultrasonic wave transmission/reception means for transmitting an ultrasonic pulse into a living body, receiving an ultrasonic echo from a living tissue, and converting the ultrasonic echo into an electric signal: movement amount detection means for analyzing a phase of the ultrasonic echo signal from the living tissue obtained by the ultrasonic wave transmission/reception means, and detecting an amount of movement of the living tissue in accordance with a body motion due to a heartbeat or a vibration; correction means for correcting an ultrasonic image signal based on the amount of movement of the living tissue detected by the movement amount detection means; and display means for displaying an image corrected by the correction means.

With this configuration, it becomes possible to provide an excellent biological signal monitor device that allows a living tissue moving in accordance with a body motion or various vibrations to be observed as if it were standing still in a display image by subjecting an ultrasonic image to reverse correction with a movement amount of the living tissue.

The first biological signal monitor device according to the present invention includes generation means for generating quasi-still image information in which a random noise component is reduced by subjecting the ultrasonic echo signal to averaging and filter processing.

With this configuration, it becomes possible to provide an excellent biological signal monitor device that can generate quasi-still image information in which a random noise component is reduced by performing averaging or various filter processing based on the fact that information from a certain region is obtained regularly without being influenced by a body motion.

In the first biological signal monitor device according to the present invention, the ultrasonic echo signal subjected to the filter processing is corrected so as to be put back to a display state where the living tissue moves in accordance with a body motion or a vibration.

With this configuration, it becomes possible to provide an excellent biological signal monitor device that can provide a clear B-mode image in which a random noise component existing in a living tissue portion moving in accordance with a body motion is reduced.

The first biological signal monitor device according to the present invention includes analysis means for extracting a boundary of a structure of the living tissue and analyzing an inner structure by using the display means that allows the living tissue moving in accordance with a body motion or a vibration to be displayed as if the living tissue were standing still.

Further, in order to achieve the above-mentioned object, a second biological signal monitor device according to the present invention includes: ultrasonic wave transmission/reception means for transmitting an ultrasonic pulse into a living body, receiving an ultrasonic echo from a living tissue, and converting the ultrasonic echo into an electric signal; movement amount detection means for analyzing a phase of the ultrasonic echo signal from the living tissue obtained by the ultrasonic wave transmission/reception means, and detecting an amount of movement of the living tissue in accordance with a body motion due to a heartbeat or a vibration; and analysis means for extracting a boundary of a structure of the living tissue and analyzing an inner structure by using the movement amount detection means.

The first and second biological signal monitor devices according to the present invention include filter processing means for subjecting a value of the boundary position of the living tissue obtained by the analysis means and values of boundary positions obtained at a plurality of places close to each other to filter processing.

With this configuration, it becomes possible to provide an excellent biological signal monitor device that can divide a boundary smoothly.

The first and second biological signal monitor devices according to the present invention include error reduction means for comparing a result of the boundary position of the living tissue obtained by the analysis means with a result of a boundary position a predetermined number or more of cycles (heartbeat cycles, for example) before, and subjecting data of the respective boundary positions to averaging processing.

With this configuration, it becomes possible to provide an excellent biological signal monitor device that can reduce an error in detecting a boundary position due to intrusion of noise.

The first and second biological signal monitor devices according to the present invention include determination means for comparing the amount of movement of the living tissue detected by the movement amount detection means with a result of detecting a movement amount a predetermined number or more of cycles (heartbeat cycles, for example) before, and determining a degree of stability (constancy) of the extraction of the boundary of the living tissue.

The first and second biological signal monitor devices according to the present invention include means for removing an image not to be monitored or changing luminance or coloration of a region to be monitored and the image not to be monitored with respect to a result of the extraction of the boundary obtained by the analysis means, thereby showing the region to be monitored clearly in a display image.

The first and second biological signal monitor devices according to the present invention include means for removing an image not to be monitored or changing luminance or coloration of a region to be monitored and the image not to be monitored with respect to a result of the extraction of the boundary obtained by the analysis means, thereby showing the region to be monitored clearly in a display image.

The first and second biological signal monitor devices according to the present invention include, in a case where a blood vessel wall is to be observed, means for obtaining a value of a blood vessel inner diameter by analyzing a structure of a blood vessel tissue based on a fact that an image in which a pulsation component due to a heartbeat is brought to a quasi-standstill and in which a random noise component is removed is obtained.

In this case, it is preferable that there is provided means for obtaining values of the blood vessel inner diameter at a plurality of places.

Further, it is preferable that there is provided means for subjecting the value of the blood vessel inner diameter to angle correction based on information on a distance between a surface of an ultrasonic probe and the blood vessel wall to be observed at a plurality of places.

Further, it is preferable that there is provided means for comparing the amount of movement of the living tissue detected by the movement amount detection means with a result of detecting a movement amount a predetermined number or more of cycles (heartbeat cycles, for example) before, and determining a degree of stability (constancy) of the measurement of the value of the blood vessel inner diameter.

Further, it is preferable that there is provided means for calculating a variation state of the value of the blood vessel inner diameter based on the obtained value of the blood vessel inner diameter and an amount of movement of the blood vessel wall in accordance with a heartbeat.

The first and second biological signal monitor devices according to the present invention include, in a case where a carotid artery is to be observed, means for obtaining an Intima Media Thickness (IMT) value as an index of arteriosclerosis by analyzing a structure of the carotid artery based on a fact that an image in which a pulsation component due to a heartbeat is brought to a quasi-standstill and in which a random noise component is removed is obtained, or a fact that the amount of movement of the living tissue in accordance with a body motion and a vibration is detected.

In this case, it is preferable that there is provided means for calculating IMT values at two or more places at the same time.

Further, it is preferable that there is provided means for displaying a region where the largest IMT value of IMT values obtained at a plurality of places is observed, in an ultrasonic image of a longitudinal cross section of a blood vessel. Further, it is preferable that there is provided means for subjecting the IMT value to angle correction based on information on a distance (depth) between an ultrasonic probe and a blood vessel wall to be observed.

Further, it is preferable that there is provided means for comparing the amount of movement of the living tissue detected by the movement amount detection means with a result of detecting a movement amount a predetermined number or more of cycles (heartbeat cycles, for example) before, and determining a degree of stability (constancy) of the measurement of the IMT value.

Further, it is preferable that there is provided means for comparing IMT values obtained at a plurality of places close to each other, and determining a degree of stability (constancy) of the measurement of the IMT value.

Further, it is preferable that there is provided means for calculating a variation state of the IMT value based on the obtained IMT value and an amount of movement of a blood vessel wall in accordance with a heartbeat.

Further, it is preferable that there are provided means for calculating a variation state of the IMT value based on the obtained IMT value and an amount of movement of a blood vessel wall in accordance with a heartbeat, and means for calculating a hardness value of an IMT measurement target region extending from a tunica intima to a tunica media based on the calculated variation amount.

Further, in order to achieve the above-mentioned object, a third biological signal monitor device according to the present invention includes: ultrasonic wave transmission/reception means for transmitting an ultrasonic pulse into a living body, receiving an ultrasonic echo from a living tissue, and converting the ultrasonic echo into an electric signal; movement amount detection means for analyzing a phase of the ultrasonic echo signal from the living tissue obtained by the ultrasonic wave transmission/reception means, and calculating an amount of movement of the living tissue in accordance with a body motion due to a heartbeat; calculation means for calculating a hardness value of the living tissue based on the amount of movement of the living tissue in a specific period; display means for displaying hardness value information two-dimensionally by using color coding based on the calculated hardness value; and means for displaying the displayed hardness value information in a state where the hardness value information is expanded or contracted so as to be in agreement with a live B-mode image based on the amount of movement of the living tissue.

The present invention can achieve the following special effect: it becomes possible to provide an excellent biological signal monitor device that can provide a live image yet allows a living tissue moving in accordance with a body motion to be observed as if it were standing still by bringing the movement of the living tissue to a quasi-standstill or performing reverse correction with a movement amount of the living tissue, can remove a random noise component existing in a living tissue portion moving in accordance with a body motion by using a general noise filter for images, and can provide a clear B-mode image in which the random noise component existing in the living tissue portion moving in accordance with a body motion is reduced by subjecting echo data from which the noise has been removed to reverse conversion into a state where the living tissue moves in accordance with a body motion.

DESCRIPTION OF THE INVENTION

Hereinafter, preferred embodiments of the present invention will be described with reference to the drawings. The following embodiments will be described by taking as an example the case of observing a carotid artery.

FIRST EMBODIMENT

Hereinafter, a first embodiment of the present invention will be described with reference to FIGS. 1 to 5 and 18.

Figure 1:
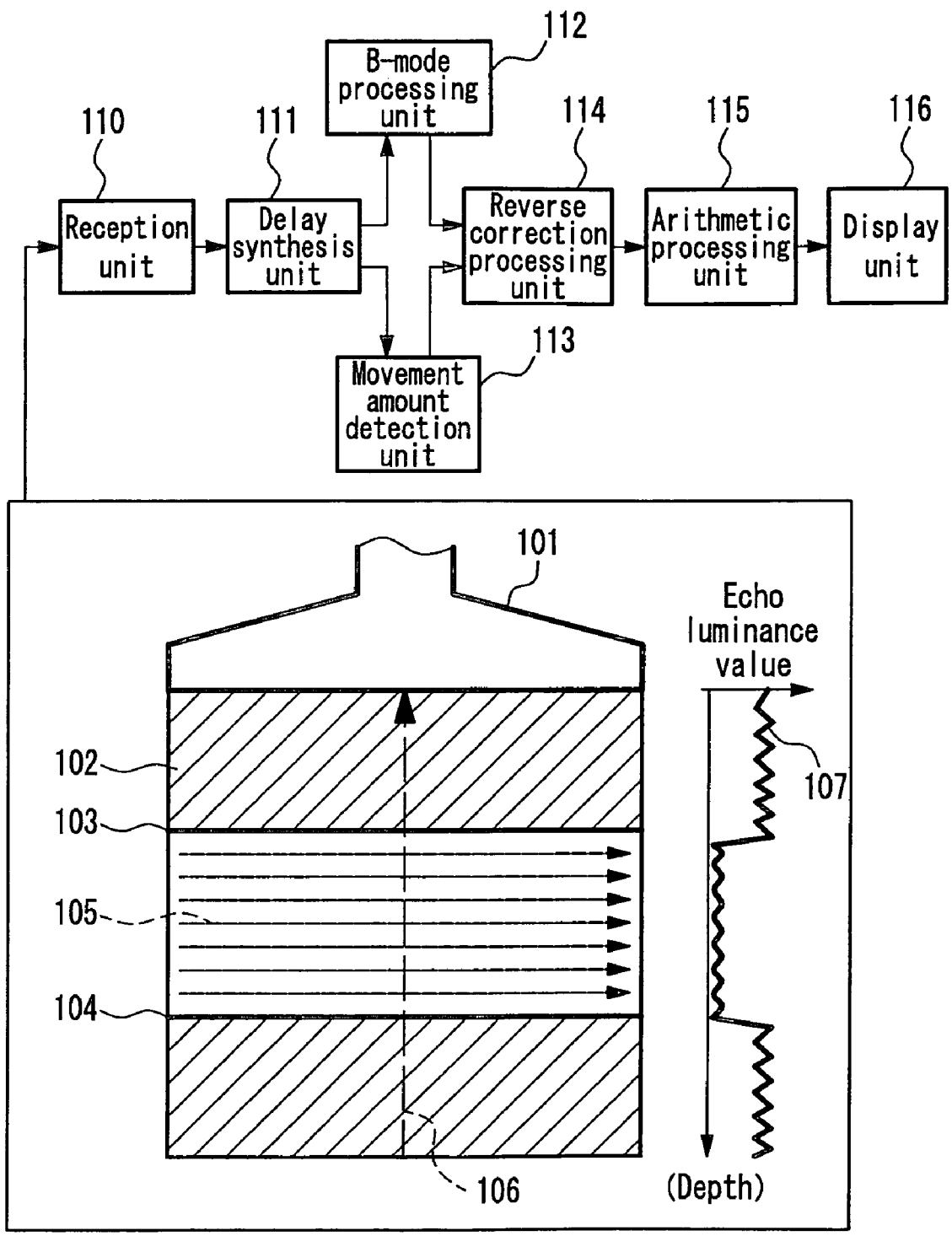
FIG. 1 is a block diagram showing an exemplary configuration of a biological signal monitor device according to a first embodiment of the present invention.

FIG. 1 is a block diagram showing an exemplary configuration of a biological signal monitor device according to the first embodiment of the present invention.

An echo signal received by an ultrasonic probe 101 is transmitted through a reception unit 110 and a delay synthesis unit 111 to a movement amount detection unit 113. The movement amount detection unit 113 detects an amount of movement of a living tissue in accordance with pulsation by a phase tracking method. Then, a reverse correction processing unit 114 as correction means cancels out (performs reverse correction) the movement amount obtained by the movement amount detection unit 113 with respect to image information from a B-mode processing unit 112, whereby a live yet quasi-still image in which a body motion component is standing still is generated. Further, an arithmetic processing unit 115 removes random noise, and a display unit 116 displays the resultant image on a monitor.

Figure 2:
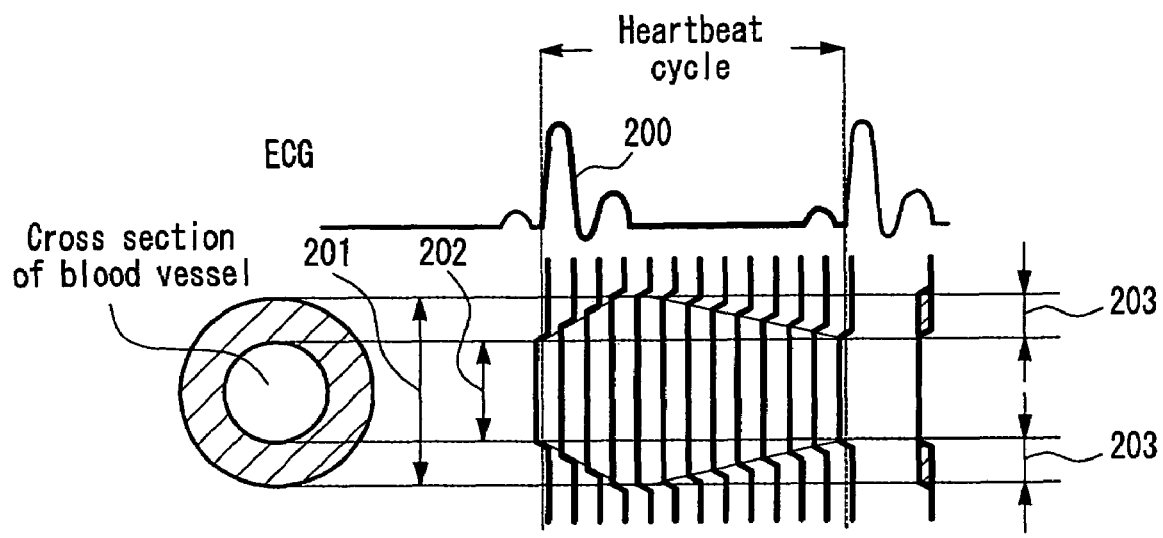
FIG. 2 is a diagram showing an echo luminance value in a state where a blood vessel wall moves in accordance with a heartbeat in the biological signal monitor device according to the first embodiment of the present invention.
Figure 3:
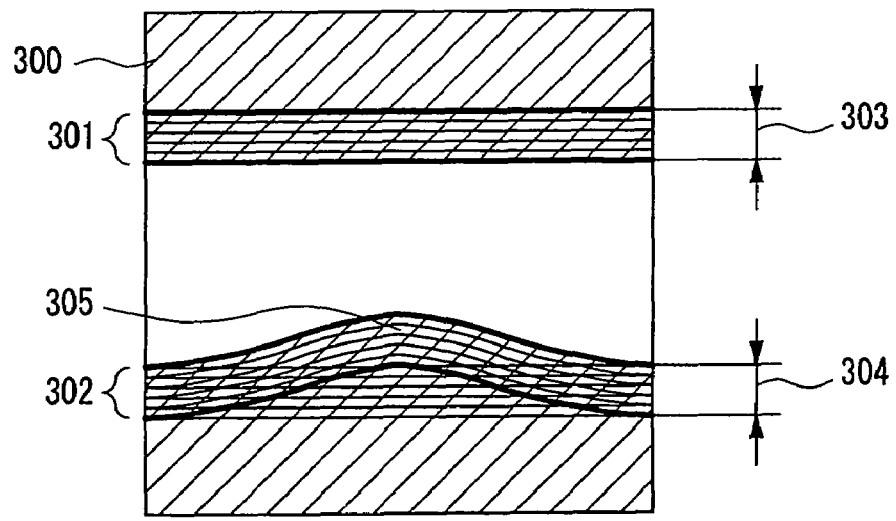
FIG. 3 is a view showing a screen displaying a B-mode image (ordinary image) in which a contour of a blood vessel wall is unclear due to a heartbeat in the biological signal monitor device according to the first embodiment of the present invention.

FIG. 2 is a diagram showing a state where an echo luminance value 107 (FIG. 1) of a reception signal obtained at a position of a scanning line 106 shown in FIG. 1 varies with a heartbeat cycle. The movement of a contour portion of a blood vessel wall can be shown by a change in boundary (step) portions of the echo luminance value 107. More specifically, in a heartbeat cycle indicated by an electrocardiogram (hereinafter, abbreviated as an "ECG") waveform 200, a cross section of a blood vessel goes through an expansion stage 201 and a contraction stage 202 repeatedly, and the blood vessel wall moves repeatedly in an area indicated by a boundary movement amount 203. In view of such variation, it is not suitable to use a live image for structural analysis of the blood vessel wall. In addition, a filter function for removing a general random noise component is not effective in the area of the boundary movement amount 203. FIG. 3 shows a state of the movement of a blood vessel wall 301, 302 in a B-mode image (ordinary image) 300 at this time. It is can be seen that a contour 303, 304 of the blood vessel wall is unclear. In particular, this shows that a live image is not suitable for use in structural analysis of an atheroma 305 or the like.

Figure 4:
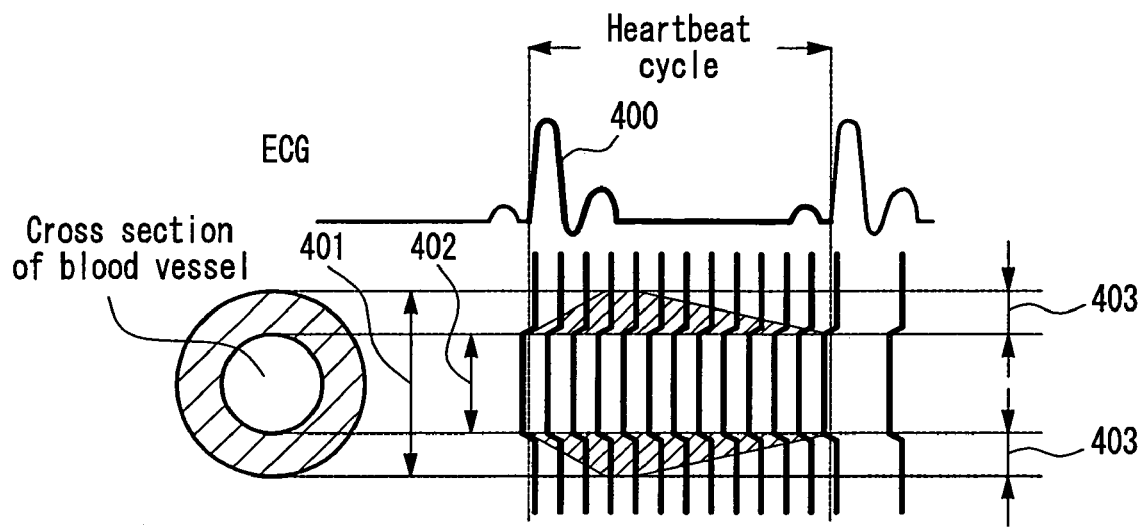
FIG. 4 is a diagram showing an echo luminance value in a state where a blood vessel wall is standing still without being influenced by a heartbeat in the biological signal monitor device according to the first embodiment of the present invention.
Figure 5:
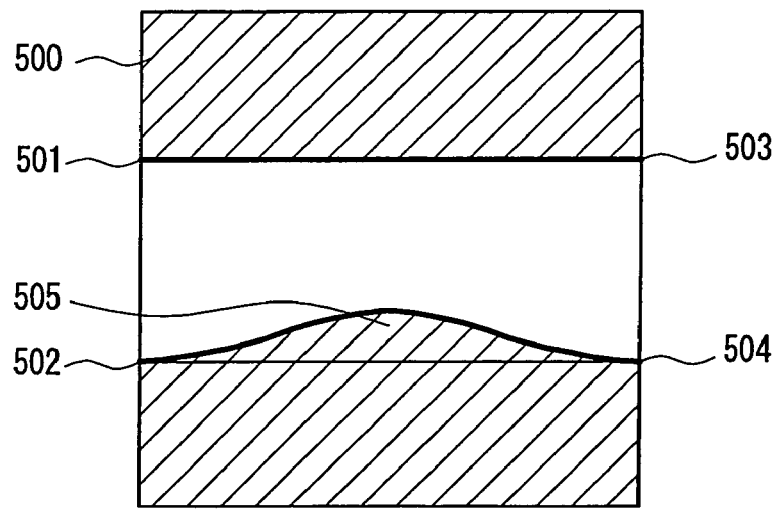
FIG. 5 is a view showing a screen displaying a B-mode image (quasi-still image) in which a contour of a blood vessel wall is clear without being influenced by a heartbeat in the biological signal monitor device according to the first embodiment of the present invention.

On the other hand, in the present embodiment, as shown in FIG. 4, a cross section of a blood vessel goes through an expansion stage 401 and a contraction stage 402 repeatedly in a heartbeat cycle shown by an ECG waveform 400. Since a movement amount of the blood vessel tissue has been calculated, the reverse correction processing unit 114 performs reverse correction with the movement amount, whereby a variation correction amount 403 is removed as a motion component. As a result, an echo luminance value does not vary with a heartbeat cycle, and thus a live yet quasi-still image in which a body motion component is standing still is generated. FIG. 5 shows a state where a blood vessel wall 501, 502 is standing still in a B-mode image (quasi-still image) 500 at this time. It can be seen that a contour 503, 504 of the blood vessel wall is clear. In particular, this shows that a live yet stable image just like a still image is obtained for structural analysis of an atheroma 505 or the like.

Further, based on the fact that information from a certain region is obtained regularly without being influenced by a body motion, it is also possible to remove a random noise component from the quasi-still image information by performing averaging or various filter processing.

Figure 18:
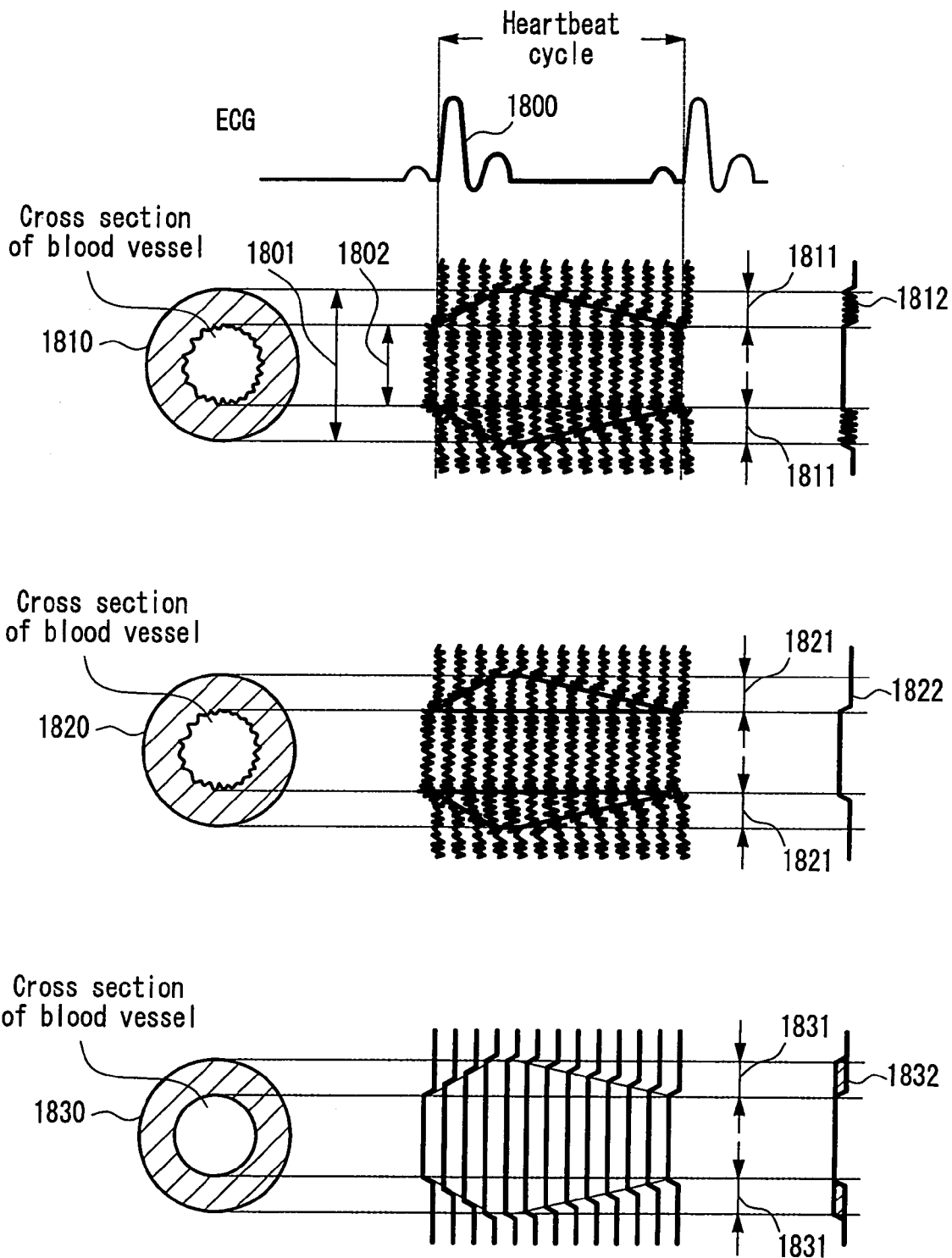
FIG. 18 is a diagram for explaining the generation of a clear B-mode image by subjecting a quasi-still image to reverse correction in the biological signal monitor device according to the first embodiment of the present invention.

FIG. 18 shows a state where echo data obtained as a result of filter processing performed in a state of the quasi-still image are subjected to reverse conversion into a state where a living tissue moves in accordance with a body motion, thereby providing a clear B-mode image in which a random noise component existing in a living tissue portion moving in accordance with a body motion is reduced.

In a heartbeat cycle indicated by an ECG waveform 1800, a cross section of a blood vessel goes through an expansion stage 1801 and a contraction stage 1802 repeatedly. Since each ultrasonic echo signal includes random noise, various filter processing is performed by a correlation operation or the like of the ultrasonic echo signal. However, in a boundary portion of a blood vessel wall 1810, a living tissue is varying as shown by a boundary movement amount 1811, and thus filter processing does not produce the usual effect on this portion. Consequently, random noise is not removed from the ultrasonic echo signal corresponding to the boundary movement portion, and noise as shown by an ultrasonic echo signal 1812 remains.

At this time, when reverse correction is performed with a movement amount of the blood vessel tissue that has been calculated, a variation correction amount 1821 of a blood vessel wall 1820 is removed as a motion component. Therefore, by performing general filter processing such as a correlation operation, an ultrasonic echo signal 1822 from which the random noise is removed can be generated.

Further, when the obtained ultrasonic echo signal 1822 is subjected to reverse conversion into a state where a living tissue moves in accordance with a body motion, it is possible to obtain an echo signal in which the random noise also is removed from a portion 1831 of a blood vessel wall 1830 moving in accordance with a body motion, as shown by an ultrasonic echo signal 1832. Therefore, when a B cross-sectional image is generated from the clear echo signal, it is possible to provide a clear B-mode image in which the random noise component existing in the living tissue portion moving in accordance with a body motion is reduced.

The invention according to the present embodiment also can be embodied three-dimensionally, and it becomes possible to recognize in real time a movement amount of a boundary tissue of a cardiac muscle wall or another internal organ that moves up and down (from side to side) in accordance with pulsation during heart surgery or the like. For example, in a remote operation or the like, when feedback about a detected movement amount is provided to an arm of a CCD camera projecting a heart or an output signal of the camera, so that the CCD camera or the output signal of the camera is moved three-dimensionally in synchronization with the movement of a cardiac muscle, the heart displayed on a monitor looks as if it were standing still, which makes it extremely easy to observe an affected area. Further, in an environment where an operating instrument such as a scalpel can be used remotely, when feedback about a detected movement is provided to a remote-control arm as well as a CCD camera, so that they are moved three-dimensionally in synchronization with the movement of a cardiac muscle, it also becomes possible to perform surgery on a beating heart as easily as in the case of treating an internal organ at a standstill, while viewing a quasi-still image displayed on a monitor.

As described above, according to the present embodiment, it becomes possible to provide an excellent biological signal monitor device that can provide a live image yet allows a living tissue moving in accordance with a body motion to be observed as if it were standing still by bringing the movement of the living tissue to a quasi-standstill or performing reverse correction with a movement amount of the living tissue, can remove a random noise component existing in a living tissue portion moving in accordance with a body motion by using a general noise filter for images, and can provide a clear B-mode image in which the random noise component existing in the living tissue portion moving in accordance with a body motion is reduced by subjecting echo data from which the noise has been removed to reverse conversion into a state where the living tissue moves in accordance with a body motion.

SECOND EMBODIMENT

Next, a second embodiment of the present invention will be described with reference to FIGS. 10, 11, and 13.

Figure 10:
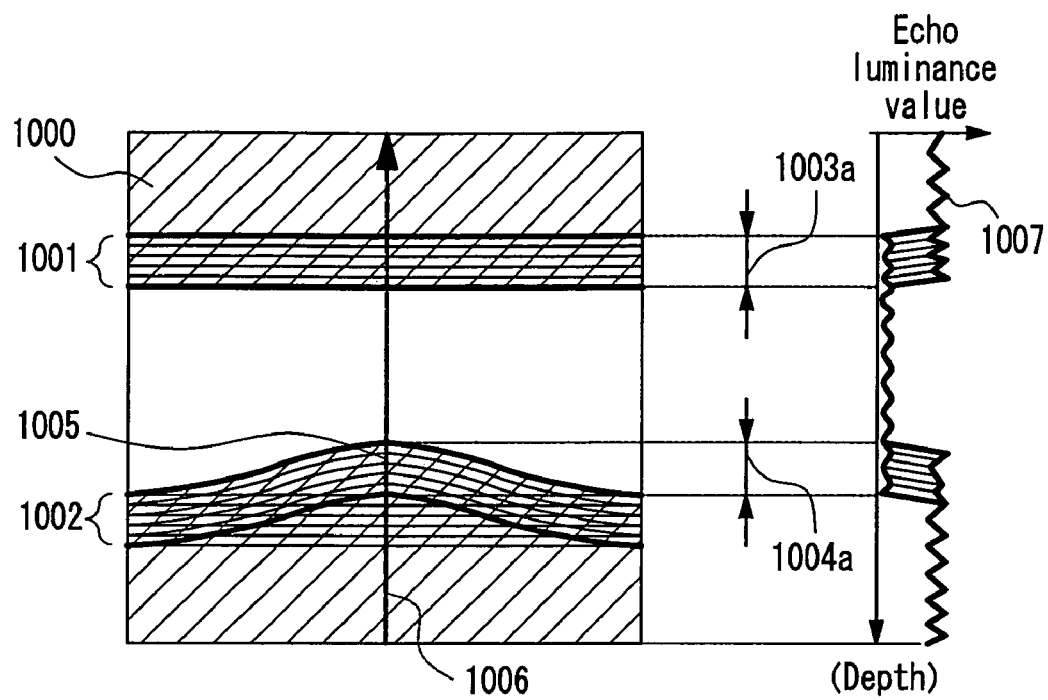
FIG. 10 is an explanatory diagram of a state where a boundary is unclear due to a body motion of a living tissue in a biological signal monitor device according to a second embodiment of the present invention.
Figure 11:
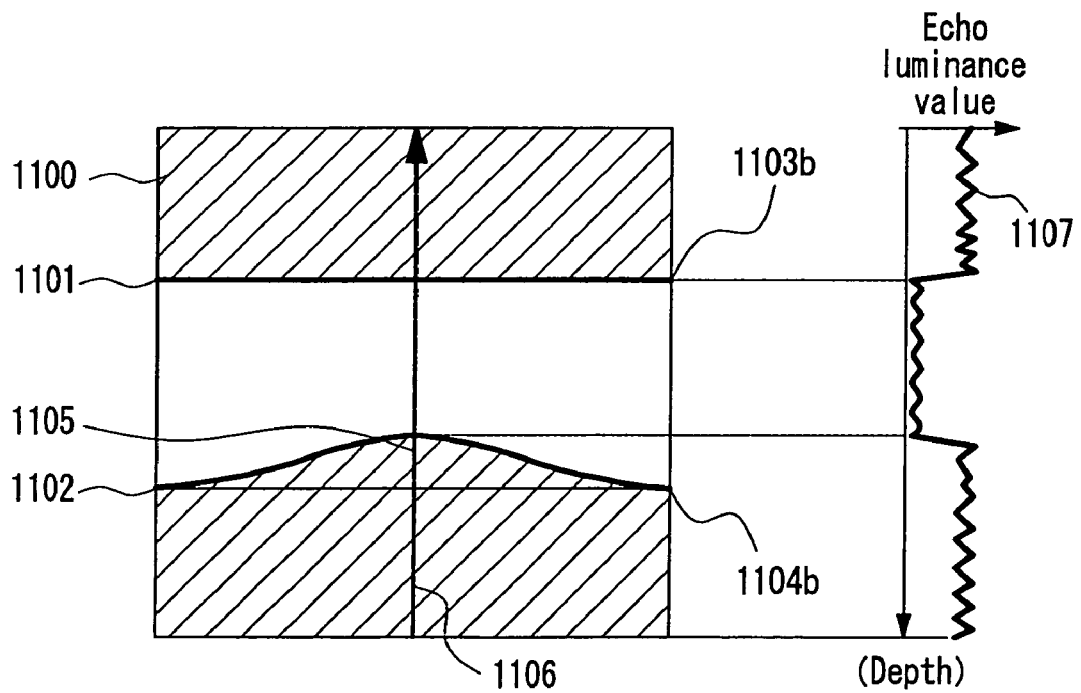
FIG. 11 is an explanatory diagram of a state where a boundary is clear with a body motion of a living tissue removed in the biological signal monitor device according to the second embodiment of the present invention.

In FIG. 10, attention is directed to a scanning line 1006. As shown in a graph of an echo luminance value 1007 of a live image, a boundary position varies with the movement of a living tissue, and accordingly it is highly likely that an error occurs when the boundary position is identified from the echo luminance value 1007. In particular, in the case of a living tissue with an atheroma 1005, which requires a precise medical diagnosis, the echo luminance value varies due to a constituent in that region and the like, and thus the luminance value of an ultrasonic echo signal is not uniform. As a result, as shown by an unclear contour 1003a, 1004a in a B-mode image 1000, it is difficult to determine a boundary position of a blood vessel wall 1001, 1002 precisely.

To solve this problem, there is provided means for analyzing the phase of the ultrasonic echo signal and calculating an amount of movement of the living tissue in accordance with a body motion such as a heartbeat or various vibrations. As a result, as shown in FIG. 11, it becomes possible to provide a quasi-still B-mode image 1100, in which an echo luminance value 1107 and a contour 1103b, 1104b are shown clearly even if an ultrasonic echo signal corresponding to a portion of the scanning line 1106 in another heartbeat is superimposed. Therefore, the boundary of a blood vessel wall 1101, 1102 can be determined precisely and easily.

Further, the arithmetic processing unit 115 (FIG. 1) may be provided with a memory for storing threshold value data for the determination of the boundary, so as to determine the boundary automatically.

Further, when the phase of the ultrasonic echo signal is analyzed, and the amount of movement of the living tissue in accordance with a body motion such as a heartbeat and various vibrations is monitored, a state in which the boundary position of the living tissue moves can be recognized even without generating a quasi-still image. Thus, similarly, the blood vessel wall 1101, 1102 can be obtained easily.

Further, when the value of the obtained boundary position of the living tissue and values of boundary positions obtained at a plurality of places close to each other are subjected to filter processing with software by the arithmetic processing unit 115 (FIG. 1), the boundary can be divided smoothly.

Further, when a threshold value at the filter processing is varied automatically in an arbitrary range, and data are extracted and stored in connection with the echo luminance value, the boundary of the living tissue can be divided more smoothly.

Figure 13:
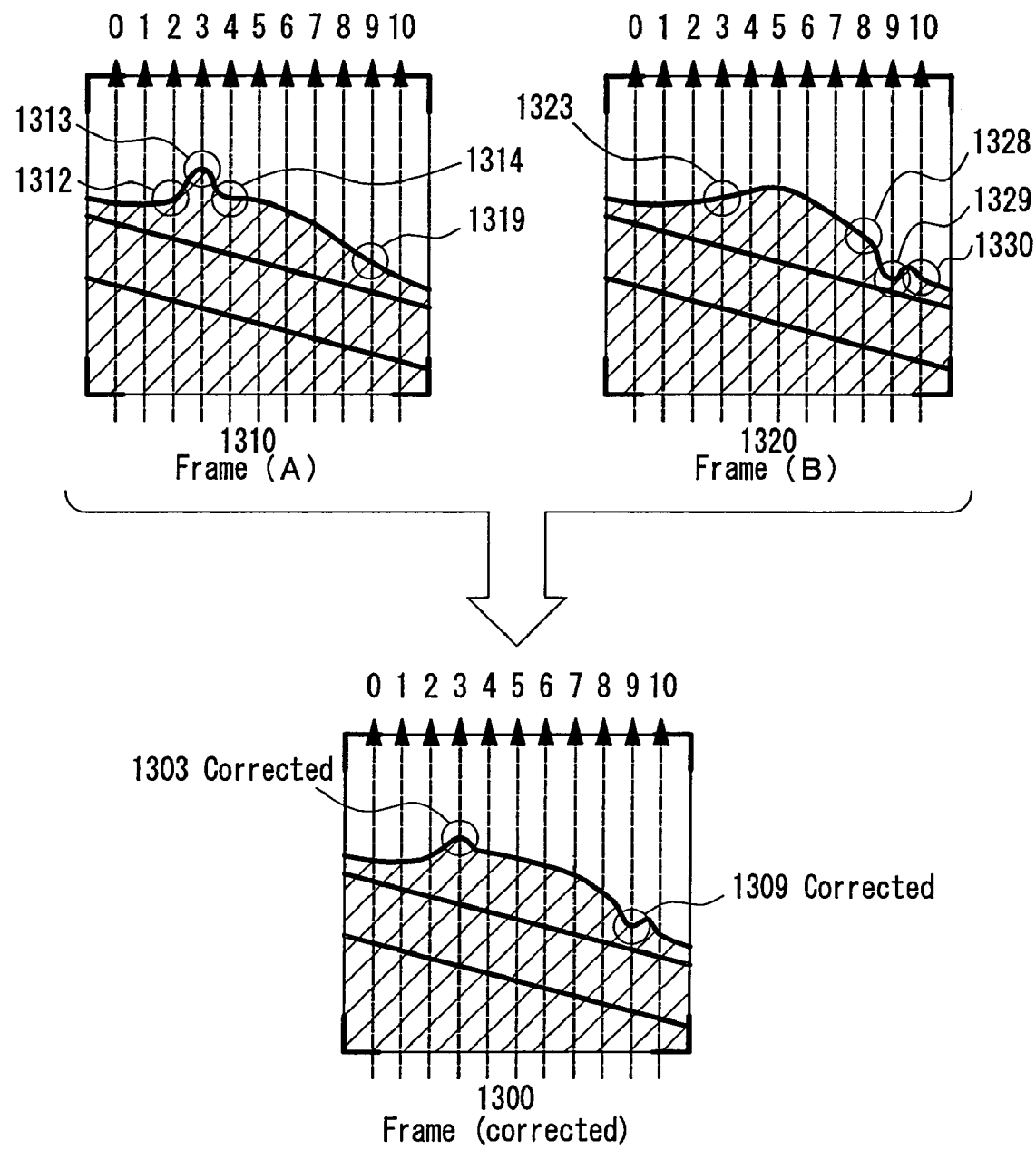
FIG. 13 is an explanatory diagram of a state where boundary positions obtained at a plurality of places are subjected to filter processing in the biological signal monitor device according to the second embodiment of the present invention.

FIG. 13 shows the result of detecting the boundary in an ROI (Region of Interest) obtained with respect to each specific cycle (for example, a heartbeat cycle), the result being shown as a frame (A) 1310 or a frame (B) 1320 in temporal order. In an actual scene of diagnosis, noise gets into tracking information on motion displacement of a blood vessel wall due to a plurality of factors such as a body motion or a respiratory state of a living body, a state in which an ultrasonic probe is fixed, and the like. As a result, noise 1313 (or noise 1329) has an influence on the detection of the boundary of the blood vessel wall. In order to minimize the influence of the noise, assuming that a boundary detection position of a position f is defined by a function of K(f), a plurality of places close to each other are subjected to filter processing as expressed by the following (Equation 1), or filter processing as expressed by the following (Equation 2) so as to make a comparison with a result obtained a predetermined number of cycles before. As a result, a boundary detection image as shown by a frame (corrected) 1300 in which the influence of the noise is minimized can be generated, as shown at corrected portions 1303 and 1309. These filter processing can be performed with software by the arithmetic processing unit 115 (FIG. 1).

$$K(1303)=\{K(1312)+K(1313)+K(1314)\}/3$$

$$K(1309)=\{K(1328)+K(1329)+K(1330)\}/3 \quad \text{(Equation 1)}$$

$$K(1303)=\{K(1313)+K(1323)\}/2$$

$$K(1309)=\{K(1319)+K(1329)\}/2 \quad \text{(Equation 2)}$$

Herein, for the sake of simplification, the two values at the places close to each other are used. However, filter processing may be performed with respect to a plurality of ranges of two or more places, which results in the same or better effect. Although the filter processing of simple averaging is performed, it is possible to change the weighting or the arithmetic expressions of the filter processing, and to combine a plurality of filter processing, resulting in the same or better effect. Further, an amplitude-displacement-motion amount of the blood vessel wall before the detection of the boundary may be subjected to various filter processing, followed by the detection of the boundary, which results in the same or better effect.

As described above, according to the present embodiment, the blood vessel wall can be obtained easily by analyzing the phase of the ultrasonic echo signal and monitoring the amount of movement of the living tissue in accordance with a body motion such as a heartbeat or various vibrations. Further, by subjecting values of boundary positions obtained at a plurality of places close to each other to filter processing, the boundary can be divided smoothly. Further, it is possible to provide an excellent biological signal monitor device that can generate a boundary detection image in which an influence of noise is minimized by subjecting a result of detecting the boundary obtained with respect to each specific cycle to filter processing or by making a comparison with a result obtained a predetermined number of cycles before.

THIRD EMBODIMENT

Next, a third embodiment of the present invention will be described with reference to FIGS. 17 and 12.

According to the present embodiment, the degree of stability (constancy) of the measurement itself for an IMT value or a value of a blood vessel inner diameter is determined with software by the arithmetic processing unit 115 (FIG. 1) based on the fact that a similar moving track of a blood vessel wall is obtained with respect to each heartbeat when ideal measurement data are obtained due to a constant positional relationship between a living body and an ultrasonic probe, a living body being in a stable state by stopping its breathing, or the like.

Figure 17:
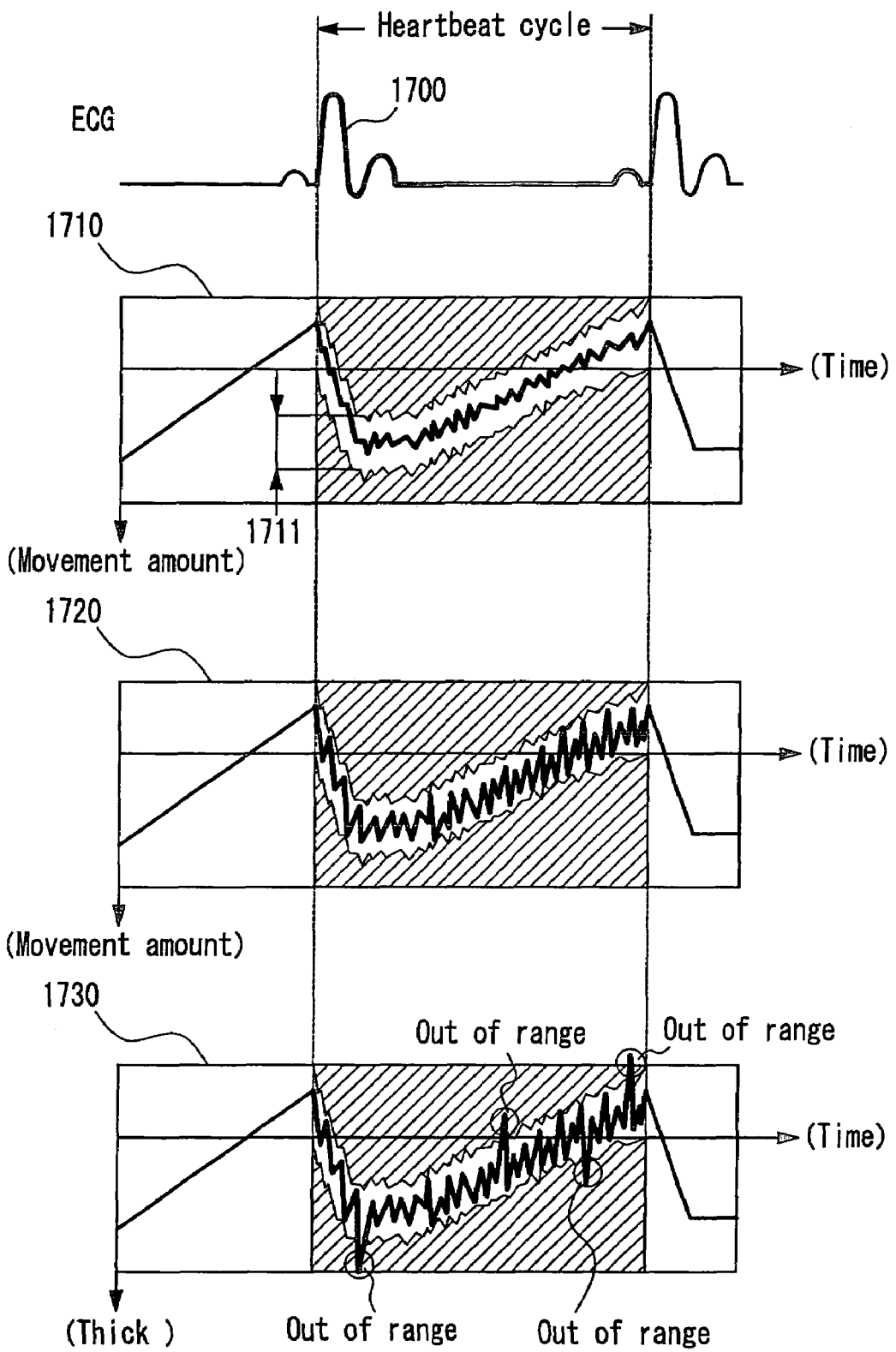
FIG. 17 is an explanatory diagram of a state where the stability of measurement is determined by comparison with a moving track in the biological signal monitor device according to the third embodiment of the present invention.

As shown in FIG. 17, for example, a region range obtained by an arbitrarily set permissible error range 1711 to a moving track 1710 in the immediately preceding cycle in synchronization with a heartbeat cycle of an ECG waveform 1700 is compared with a track in the subsequent measuring cycle. When the track is within the permissible error range 1711 at any points as shown by a track 1720 in stable measurement, it is determined that stable measurement has been performed. On the other hand, when the track falls outside the permissible error range at some points as shown by a track 1730 in unstable measurement, it is determined that unstable measurement has been performed. When a measurer is notified of this information in real time, the measurer can determine during the measurement whether the present measurement result is reliable or not. As a result, a measuring time can be expected to be shorter.

Of course, the comparison may be made with the immediately preceding cycle for a difference therefrom or may be made with a stable track obtained not only from the immediately preceding cycle but also from a plurality of past cycles, which results in the same effect. Further, a better effect can be obtained by varying a threshold value for distinguishing between stable measurement and unstable measurement. The same effect also can be obtained by comparing a value (for example, a pseudo boundary determination position or the like) obtained from an echo luminance value unsuitable for determining a boundary in the immediately preceding cycle with that in the present cycle. Further, it is possible to combine a plurality of functions for determining the degree of measurement stability, such as comparing the degrees of approximation between IMT values at a plurality of places close to each other based on the fact that IMT values at a plurality of places close to each other in terms of the structure of a living body are approximate to each other. As a result, a threshold value for determining stable measurement is raised, and the reliability of a measurement result can be improved further.

Figure 12:
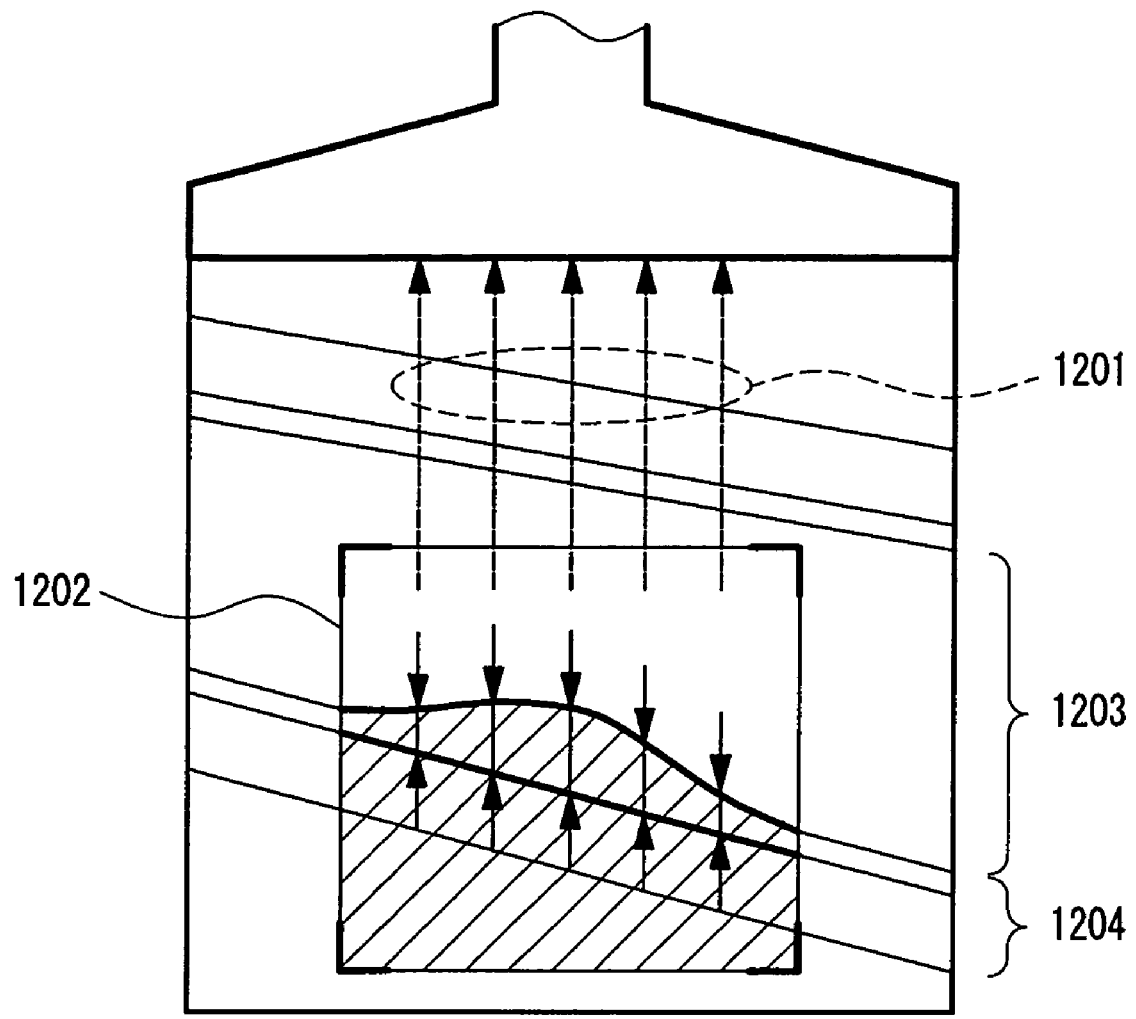
FIG. 12 is an explanatory diagram of a state where a boundary is detected at a plurality of places, so that a Region of Interest is divided in a biological signal monitor device according to a third embodiment of the present invention.

Further, as shown in FIG. 12, when a boundary is detected with respect to a plurality of scanning lines (N scanning lines) as in the second embodiment, information from a blood flow portion 1203 and information from a blood vessel wall 1204 in an ROI (Region of Interest) 1202 can be separated from each other. Therefore, in a medical diagnosis, it becomes possible to remove a noise component from an unwanted blood flow portion or the like in a two-dimensional image, or to generate an image obtained by subjecting each living tissue such as the blood flow portion 1203, the blood vessel wall 1204, and the like to processing for changing the luminance or the coloration thereof or the like.

As described above, according to the present embodiment, it is possible to determine the degree of stability (constancy) of the measurement itself for an IMT value or a value of a blood vessel inner diameter. When a measurer is notified of this information in real time, the measurer can determine during the measurement whether the present measurement result is reliable or not. As a result, a measuring time can be expected to be shorter.

Further, it is possible to combine a plurality of functions for determining the degree of measurement stability, such as comparing the degrees of approximation between IMT values at a plurality of places close to each other based on the fact that IMT values at a plurality of places close to each other in terms of the structure of a living body are approximate to each other. As a result, a threshold value for determining stable measurement is raised, and the reliability of a measurement result can be improved further.

Further, by detecting a boundary, in a medical diagnosis, it is possible to remove a noise component from an unwanted blood flow portion or the like in a two-dimensional image, or to generate an image obtained by subjecting each living tissue such as the blood flow portion, the blood vessel wall, and the like to processing for changing the luminance or the coloration thereof or the like.

Therefore, it becomes possible to provide an excellent biological signal monitor device having the above-mentioned advantages.

FOURTH EMBODIMENT

Next, a fourth embodiment of the present invention will be described with reference to FIGS. 19, 20, and 14.

Figure 19:
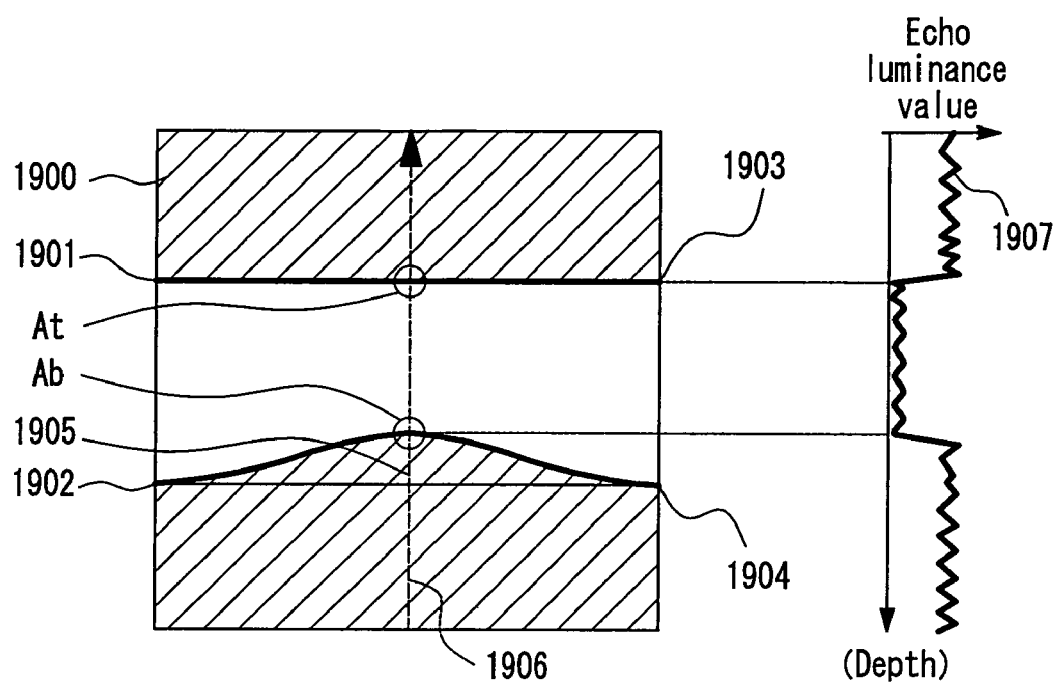
FIG. 19 is an explanatory diagram of a state where a value of a blood vessel inner diameter is obtained by detecting boundaries in the biological signal monitor device according to the fourth embodiment of the present invention.

As shown in FIG. 19, when boundaries of an anterior wall 1901 and a posterior wall 1902 of a blood vessel are detected to show clear contours 1903 and 1904 as in the second embodiment, boundary positions At and Ab on a scanning line 1906 can be located. At the same time, since the depth of each of the boundary positions At and Ab is recognized, a value of a blood vessel inner diameter can be obtained easily by the arithmetic processing unit 115 (FIG. 1) obtaining a difference between information on the depths of the boundary positions At and Ab.

Further, for example, by moving an aperture by linear-array-type ultrasonic wave transmission/reception means, values of the blood vessel inner diameter at a plurality of places, in addition to the value on the scanning line 1906, also can be obtained at the same time.

Figure 14:
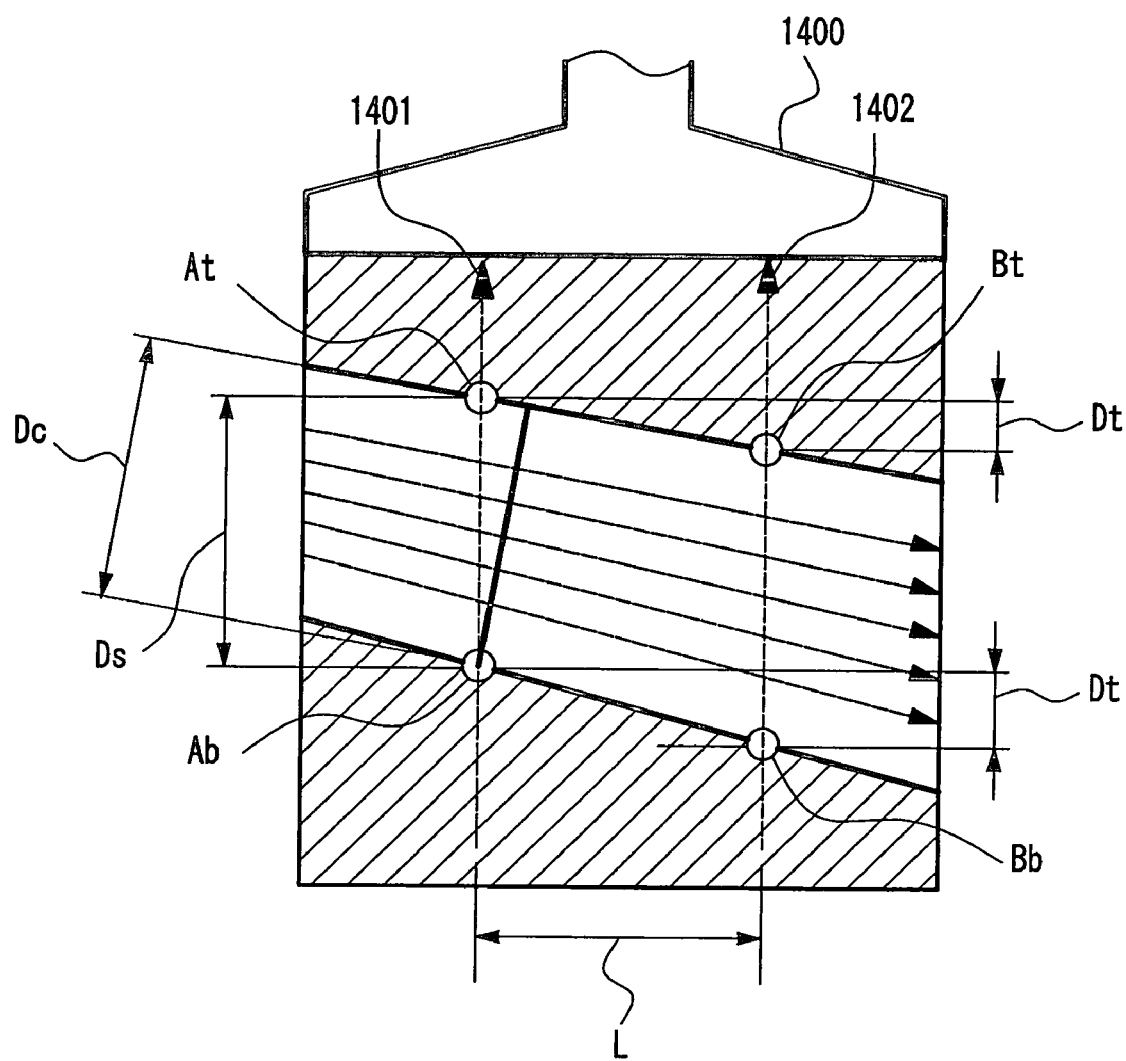
FIG. 14 is an explanatory diagram of angle correction of an IMT value in a biological signal monitor device according to a fourth embodiment of the present invention.

Further, FIG. 14 shows that the value of the blood vessel inner diameter can be subjected to angle correction by using the position information of the blood vessel wall whose boundary has been determined by using a quasi-still image in which a body motion component is removed.

Reference numeral 1400 denotes an ultrasonic probe, 1401 denotes a scanning line (A), and 1402 denotes a scanning line (B). A point Ab is a boundary position of a blood vessel wall on the scanning line (A) 1401, and a point Bb is a boundary position of the blood vessel wall on the scanning line (B) 1402. Db denotes a depth difference between the points Ab and Bb, L denotes a parallel distance between the scanning line (A) 1401 and the scanning line (B) 1402, and Ds denotes a distance between the points At and Ab, i.e., a value of the inner diameter before angle correction. A value Dc of the blood vessel inner diameter, which is a value obtained as a result of subjecting the value Ds of the blood vessel inner diameter on the scanning line (A) 1401 to angle correction, can be obtained by the following (Equation 3).

$$Dc = Ds \times \cos\{a\tan(Db/L)\} \qquad \text{(Equation 3)}$$

Of course, it is also possible to use a depth difference Dt between the points At and Bt as tunica intima positions on a side closer to a body surface, thereby increasing the accuracy of the angle correction further.

Further, as in the third embodiment, it is also possible to compare a movement amount of a living tissue detected by the movement amount detection unit 113 (FIG. 1) with a result of detecting a movement amount a predetermined number or more of cycles (heartbeat cycles, for example) before, thereby determining the degree of stability (constancy) of the measurement of the value of the blood vessel inner diameter.

Figure 20:
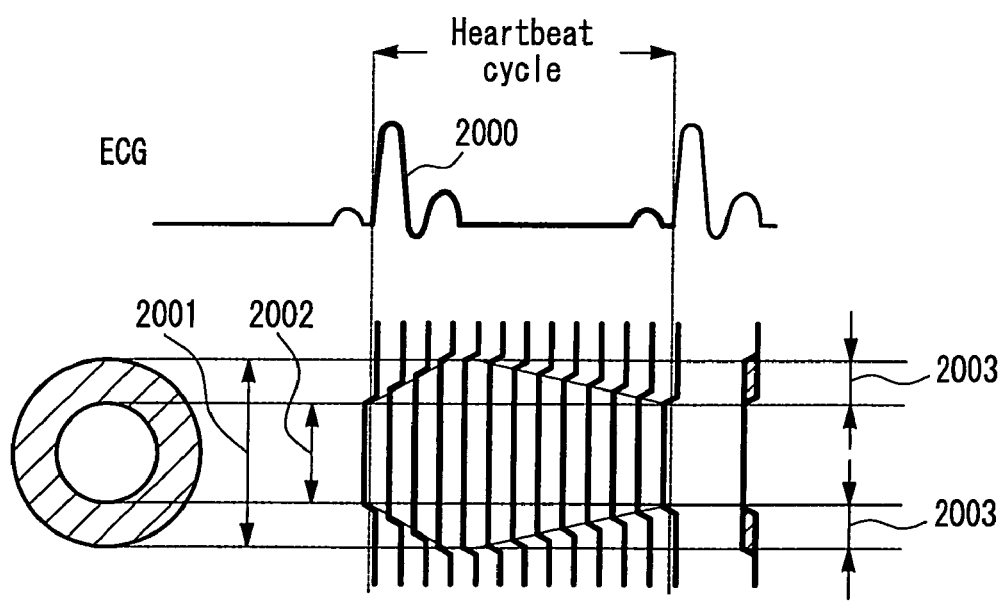
FIG. 20 is an explanatory diagram of a state where a value of a blood vessel inner diameter varies with a heartbeat in the biological signal monitor device according to the fourth embodiment of the present invention.

Further, as shown in FIG. 20, when the value of the blood vessel inner diameter in synchronization with a heartbeat cycle of an ECG waveform 2000 is observed for a single heartbeat period or more, it is possible to calculate a variation state of the value of the blood vessel inner diameter, such as an inner diameter value 2001 in an expansion stage, an inner diameter value 2002 in a contraction stage, and the like in addition to a boundary movement amount 2003. Thus, it also becomes possible to obtain an inner diameter variation parameter, which is useful for a diagnosis of arteriosclerosis and the like.

As described above, according to the present embodiment, it is possible to obtain the value of the blood vessel inner diameter easily, and also to obtain values of the blood vessel inner diameter at a plurality of places at the same time. Further, it is possible to subject the value of the blood vessel inner diameter to angle correction, and also to determine the degree of stability (constancy) of the measurement of the value of the blood vessel inner diameter by comparing a movement amount with a result of detecting a movement amount a predetermined number or more of cycles (heartbeat cycles, for example) before. Further, when the value of the blood vessel inner diameter in synchronization with a heartbeat cycle is observed for a single heartbeat period or more, a variation state of the value of the blood vessel inner diameter can be calculated. Thus, it becomes possible to provide an excellent biological signal monitor device that can obtain an inner diameter variation parameter, which is useful for a diagnosis of arteriosclerosis and the like.

FIFTH EMBODIMENT

Figure 15:
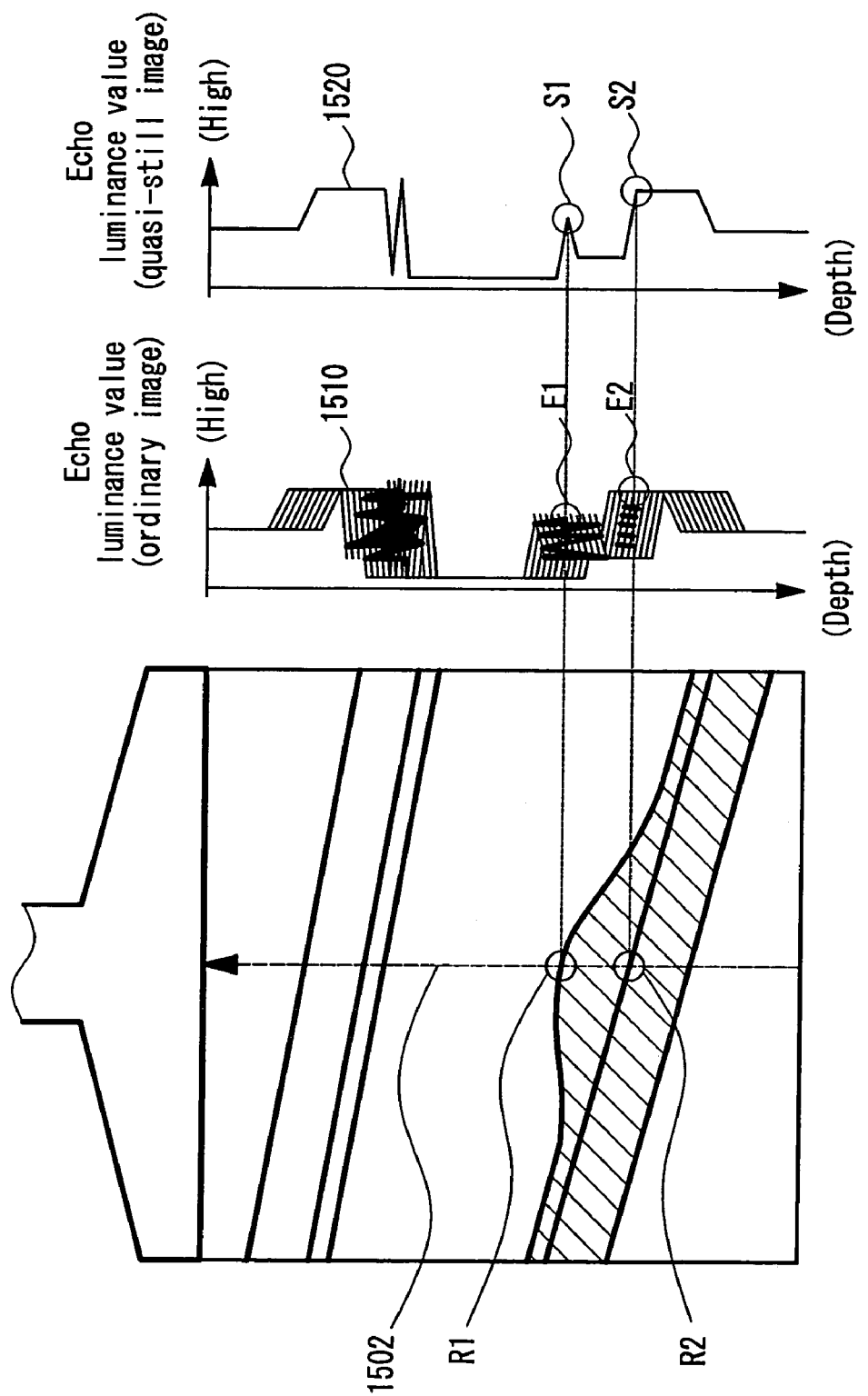
FIG. 15 is an explanatory diagram of the detection of boundaries for obtaining an IMT value in a biological signal monitor device according to a fifth embodiment of the present invention.

Next, a fifth embodiment of the present invention will be described with reference to FIGS. 15 and 16.

To measure an IMT value by using a luminance value of an ultrasonic echo signal, it is required, based on the assumption that a blood vessel wall has a standard structure in which a tunica intima boundary has luminance lower than that of a tunica media boundary, that two threshold values be set, and that two boundary positions, i.e., the boundary of a tunica intima portion and the boundary of a tunica media portion be obtained. In FIG. 15, attention is directed to a distance between a point R1 and a point R2 as a blood vessel wall on a scanning line 1502. As shown in a graph of echo luminance 1510 of a reception signal, boundary positions on points E1 and E2 vary with the movement of a living tissue, and thus it is highly likely that an error occurs when the boundary positions are identified from the echo luminance value 1510 of an ordinary image. On the other hand, as shown in a graph of echo luminance 1520 of a quasi-still image, a contour of the blood vessel wall is shown clearly as on points S1 and S2 in an image in which a movement amount of a living body is corrected. Thus, it is possible for the arithmetic processing unit 115 (FIG. 1) to determine the boundaries with software precisely and easily. Consequently, by obtaining the distance between the tunica intima and the tunica media, it is possible to provide an IMT value.

Similarly, IMT values at two or more places can be obtained at the same time. In a scene of medical treatment, the largest IMT value in a blood vessel often is used for a diagnosis. In view of this, a region where the largest IMT value of IMT values calculated at a plurality of places is observed can be displayed in an ultrasonic image on a monitor, and the numerical value thereof also can be displayed. Further, in the case where a blood vessel image is not parallel to a body surface, the IMT value can be subjected to angle correction in the same manner as that for a value of a blood vessel inner diameter.

Further, it is also possible to determine the degree of stability (constancy) of the measurement of the IMT value by comparing a movement amount of a living tissue detected by the movement amount detection unit 113 (FIG. 1) with a result of detecting a movement amount a predetermined number or more of cycles (heartbeat cycles, for example) before, or to determine the degree of stability (constancy) of the measurement of the IMT value by comparing IMT values obtained at a plurality of places close to each other.

Figure 16:
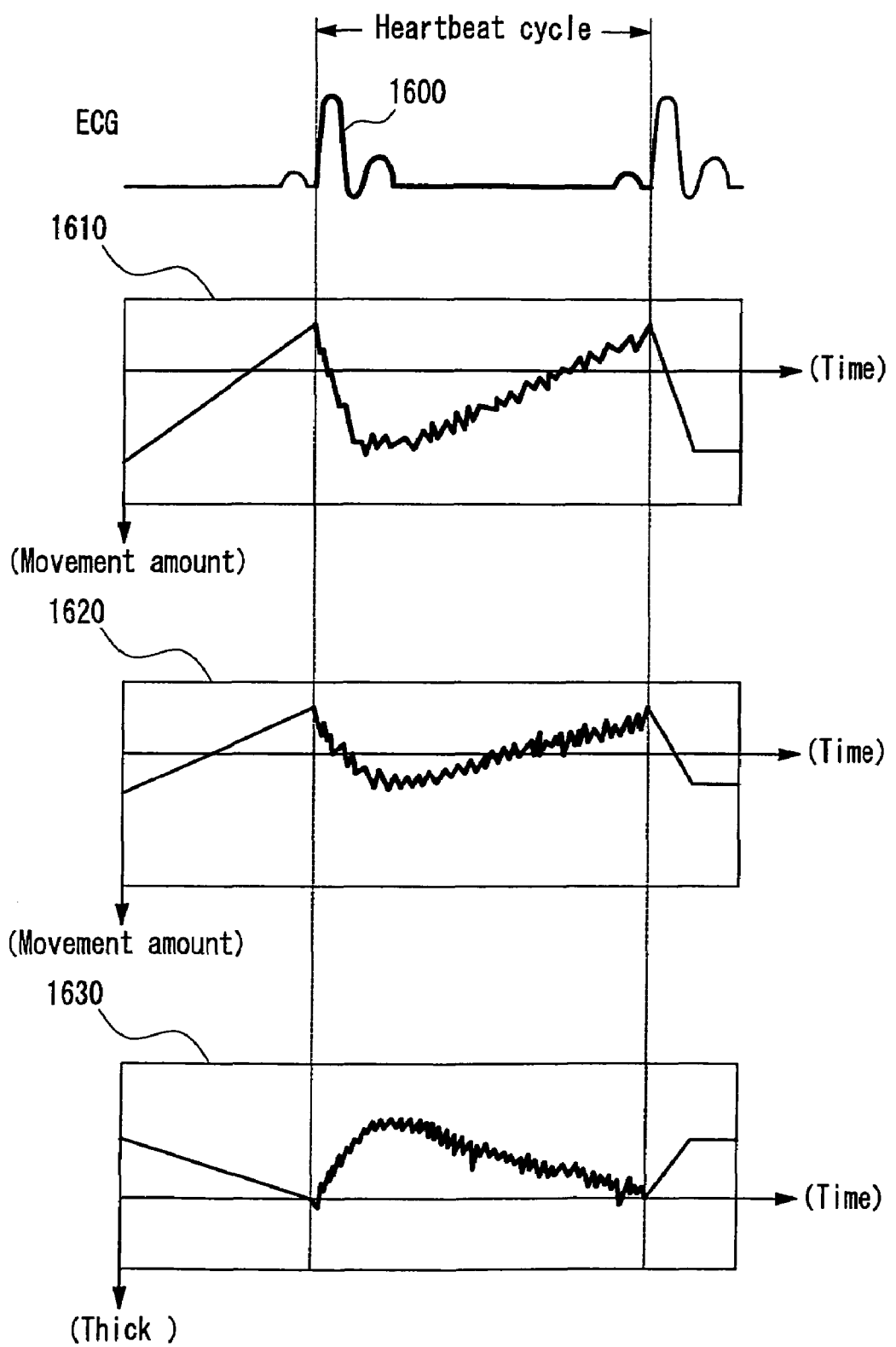
FIG. 16 is an explanatory diagram of a state where an IMT value varies with a heartbeat in the biological signal monitor device according to the fifth embodiment of the present invention.

Further, by observing the IMT value for a certain period or more, it is possible to calculate a hardness value (the elastic modulus, the viscosity, the bonding property of a tissue, or the like) as a living tissue, a variation state of the IMT value, a hardness value of an IMT portion, and the like from, for example, the magnitude of a movement amount of a target region in a heartbeat cycle of an ECG waveform 1600 in FIG. 16, a peak delay time, and the like. For example, when a movement amount shown by a track 1610 of a tunica intima movement amount in synchronization with the heartbeat cycle of the ECG waveform 1600 in FIG. 16 is compared with a movement amount shown by a track 1620 of a tunica media movement amount, it can be seen that the tunica media movement amount is smaller than the tunica intima movement amount. This shows that a hardness value of the tissue from the tunica intima to the tunica media as an IMT range is low, in other words, the tissue is soft, and accordingly when a pressure in a blood vessel is changed in accordance with a heartbeat, the IMT value decreases with increasing pressure as shown by a track 1630 of (tunica intima movement amount)−(tunica media movement amount). Therefore, by observing a heartbeat base time (R-wave time, for example), it is possible to recognize a variation amount and a variation state of the IMT value, such as the maximum value, the minimum value, an average value, and the like in a single heartbeat period.

Further, the hardness value (Er) of the IMT measurement target region can be calculated by the following (Equation 4), for example, based on the observation data on the variation state of the IMT value in the heartbeat base time.

$Er=$(IMT value in $R$-wave time)/(variation amount of IMT value)     (Equation 4)

As described above, according to the present embodiment, it is possible to determine the boundaries precisely and easily in an image in which a movement amount of a living body is corrected, and to calculate the IMT value by obtaining the distance between the tunica intima and the tunica media. Further, IMT values at two or more places can be obtained at the same time. Further, since the largest IMT value in a blood vessel often is used for a diagnosis in a scene of medical treatment, a region where the largest IMT value of IMT values calculated at a plurality of places is observed can be displayed in an ultrasonic image on a monitor, and the numerical value thereof can be displayed. Further, in the case where a blood vessel image is not parallel to a body surface, the IMT value can be subjected to angle correction in the same manner as that for a value of a blood vessel inner diameter. Further, it is also possible to determine the degree of stability (constancy) of the measurement of the IMT value by making a comparison with a result of measuring a change with time a predetermined number or more of cycles (heartbeat cycles, for example) before, or to determine the degree of stability (constancy) of the measurement of the IMT value by comparing IMT values obtained at a plurality of places close to each other. Moreover, by observing a heartbeat base time (R-wave time, for example), it is possible to recognize a variation amount and a variation state of the IMT value, such as the maximum value, the minimum value, an average value, and the like in a single heartbeat period. Further, it becomes possible to provide an excellent biological signal monitor device that can calculate the hardness value of the IMT measurement target region based on the observation data on the variation state of the IMT value in the heartbeat base time.

SIXTH EMBODIMENT

Next, a sixth embodiment of the present invention will be described with reference to FIGS. 6 to 9. In the present embodiment, a description will be given of the case where a hardness value of a living tissue is displayed in a B-mode image by means of a color display or the like so as to be superimposed on the B-mode image based on a movement amount of the living tissue obtained in a specific heartbeat cycle.

Figure 6:
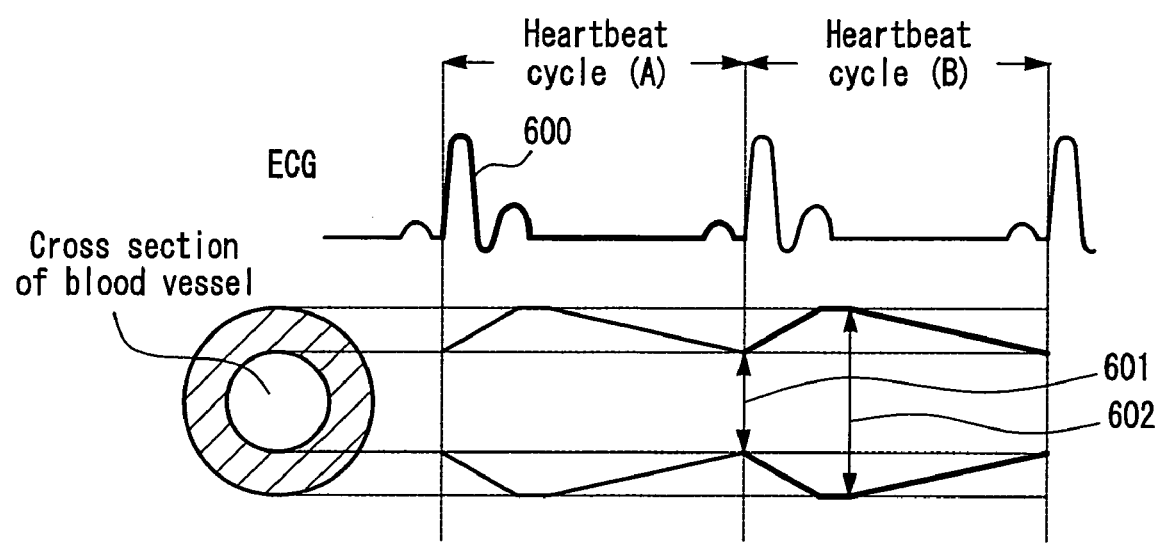
FIG. 6 is a diagram showing a state where a blood vessel wall moves in accordance with a heartbeat in a biological signal monitor device according to a sixth embodiment of the present invention.
Figure 7:
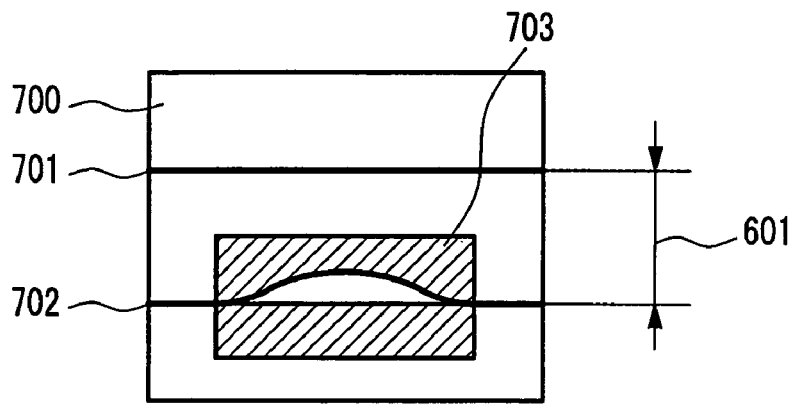
FIG. 7 is a view showing a screen displaying a B-mode image and a hardness value display region when a blood vessel wall is in a contraction stage in the biological signal monitor device according to the sixth embodiment of the present invention.

As shown in FIG. 6, a cross section of a blood vessel goes through a contraction stage 601 and an expansion stage 602 repeatedly in a heartbeat cycle (A) and a heartbeat cycle (B), respectively, shown by an ECG waveform 600. A B-mode image at the contraction stage 603 corresponds to an image 700 at a contraction stage shown in FIG. 7. In FIG. 7, the distance between a blood vessel wall 701 and a blood vessel wall 702 becomes minimum, and hardness value information of a living tissue calculated in the period of the heartbeat cycle (A) is subjected to color display in a hardness value display region 703. The B-mode image 700 and the hardness value information are in agreement with each other in position and size.

Figure 8:
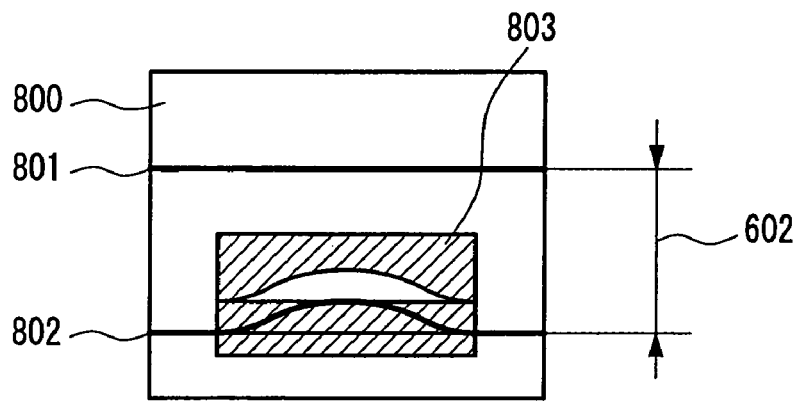
FIG. 8 is a view showing a screen displaying a B-mode image and a hardness value display region that are in disagreement with each other when a blood vessel wall is in an expansion stage in the biological signal monitor device according to the sixth embodiment of the present invention.

On the other hand, as shown in FIG. 8, a B-mode image at the expansion stage 602 of the cross section of the blood vessel corresponds to an image 800 at an expansion stage. The distance between a blood vessel wall 801 and a blood vessel wall 802 becomes maximum. When the hardness value information of the living tissue calculated in the period of the heartbeat cycle (A) is subjected to color display in a hardness value display region 803, the B-mode image and the hardness value information are in disagreement with each other in position and size.

Figure 9:
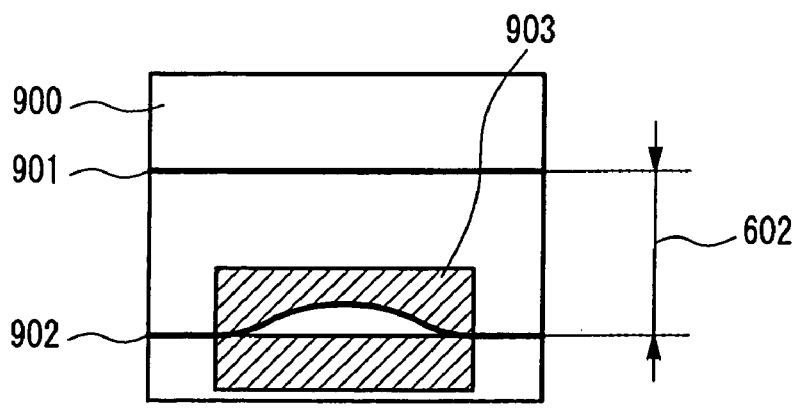
FIG. 9 is a view showing a screen displaying a B-mode image and a hardness value display region that are in agreement with each other even in an expansion stage in the biological signal monitor device according to the sixth embodiment of the present invention.

In order to solve the this problem, the display position of the hardness value information of the living tissue calculated in the period of the heartbeat cycle (A) is subjected to correction based on movement information of the living tissue obtained in the heartbeat cycle (B). As a result, as shown in FIG. 9, the B-mode image corresponds to an image 900 at an expansion stage. In this manner, even in the case where the distance between a blood vessel wall 901 and a blood vessel wall 902 becomes maximum, when the hardness value information is subjected to color display in a hardness value display region 903 in a state where the position and the size of the hardness value information of the living tissue calculated in the period of the heartbeat cycle (A) are corrected, the B-mode image and the hardness value information are in agreement with each other in position and size regardless of a movement state of the blood vessel wall in accordance with a heartbeat cycle.

Of course, even in a state where the contraction stage is changing to the expansion stage or a state where the expansion stage is changing to the contraction stage, the position and the size of each of the B-mode image and the hardness value information are in agreement with a movement state of the blood vessel wall in accordance with a heartbeat cycle.

As described above, according to the present embodiment, it becomes possible to provide an excellent biological signal monitor device having the following advantage. That is, even when the hardness value information of a living tissue is displayed in a B-mode image by means of a color display or the like so as to be superimposed on the B-mode image based on a movement amount of the living tissue obtained in a specific heartbeat cycle, the display region for the hardness value information can be located in a place in agreement with the position and the size of the living tissue moving constantly in accordance with a body motion in a B-mode image, by subjecting the display position of the hardness value information of the living tissue to correction based on the movement information of the living tissue.

INDUSTRIAL APPLICABILITY

The biological signal monitor device according to the present invention has advantages that it is possible to provide a live image yet allows a living tissue moving in accordance with a body motion to be observed as if it were standing still by bringing the movement of the living tissue to a quasi-standstill or performing reverse correction with a movement amount of the living tissue, that it is possible to remove a random noise component existing in a living tissue portion moving in accordance with a body motion by using a general noise filter for images, and that it is possible to provide a clear B-mode image in which the random noise component existing in the living tissue portion moving in accordance with a body motion is reduced by subjecting echo data from which the noise has been removed to reverse conversion into a state where the living tissue moves in accordance with a body motion. This biological signal monitor device can be applied to a diagnostic medical treatment and the like.

The invention claimed is:

1. A biological signal monitor device, comprising:
an ultrasonic wave transmission/reception unit for transmitting first and second ultrasonic pulses time sequentially into a living body, receiving first and second ultrasonic echo signals from a living tissue, and converting the ultrasonic echo signals into electric signals;
a movement amount detection unit for analyzing a phase of the ultrasonic echo signals from the living tissue obtained by the ultrasonic wave transmission/reception unit, wherein analyzing the phase of the ultrasonic echo signals includes detecting an amount of a phase shift between the ultrasonic echo signals, and detecting an amount of movement of the living tissue in accordance with a body motion due to a heartbeat or a vibration, wherein detecting the amount of movement includes converting the amount of the phase shift into a distance;
a correction unit for correcting the ultrasonic echo image signals based on the amount of movement of the living tissue detected by the movement amount detection unit in order to perform reverse correction with the amount of movement, thereby removing a variation due to the movement, resulting in reverse corrected ultrasonic echo signals;
a generation unit for subjecting the reverse corrected ultrasonic echo signals to averaging and filter processing, thereby generating filter-processed ultrasonic echo signals, wherein a random noise component is reduced from the reverse corrected ultrasonic echo signals;
a reverse conversion unit for subjecting the filter-processed ultrasonic echo signals to reverse conversion so as to be put back to a state where an image of the living tissue moves in accordance with a body motion or a vibration; and
a display unit for displaying the image based on the reverse converted ultrasonic echo signals.

2. A biological signal monitor device comprising:
an ultrasonic wave transmission/reception unit for transmitting first and second ultrasonic pulses time sequentially into a living body, receiving first and second ultrasonic echo signals from a living tissue, and converting the ultrasonic echo signals into electric signals;
a movement amount detection unit for analyzing a phase of the ultrasonic echo signals from the living tissue obtained by the ultrasonic wave transmission/reception unit, wherein analyzing the phase of the ultrasonic echo signals includes detecting an amount of a phase shift between ultrasonic echo signals, and detecting an amount of movement of the living tissue in accordance with a body motion due to a heartbeat or a vibration, wherein detecting the amount of movement includes converting the amount of the phase shift into a distance;
a correction unit for correcting the ultrasonic echo signals based on the amount of movement of the living tissue detected by the movement amount detection unit in order to perform reverse correction with the amount of movement, thereby removing a variation due to the movement; and
a display unit for displaying an image corrected by the correction unit;
an analysis unit for extracting a boundary of a structure of the living tissue and analyzing an inner structure by using the display unit that allows the living tissue moving in accordance with a body motion or a vibration to be displayed as if the living tissue were standing still; and
a determination unit for determining a degree of stability of the extraction of the boundary of the living tissue based on comparison of the amount of movement of the living tissue detected by the movement amount detection unit with a result of detecting a movement amount a predetermined number or more of cycles before.

3. The biological signal monitor device according to claim 2, comprising a filter processing unit for subjecting a value of the boundary position of the living tissue obtained by the analysis unit and values of boundary positions obtained at a plurality of places close to each other to filter processing.

4. The biological signal monitor device according to claim 2, comprising an error reduction unit for comparing a result of the boundary position of the living tissue obtained by the analysis unit with a result of a boundary position a predetermined number or more of cycles before, and subjecting data of the respective boundary positions to averaging processing.

5. The biological signal monitor device according to claim 2, comprising a unit for removing an image not to be monitored or changing luminance or coloration of a region to be monitored and the image not to be monitored with respect to a result of the extraction of the boundary obtained by the analysis unit, thereby showing the region to be monitored clearly on a display image.

6. The biological signal monitor device according to claim 2, comprising, in a case where a blood vessel wall is to be observed, a unit for obtaining a value of a blood vessel inner diameter by analyzing a structure of a blood vessel tissue based on a fact that an image in which a pulsation component due to a heartbeat is brought to a quasi-standstill and in which a random noise component is removed is obtained.

7. The biological signal monitor device according to claim 6, comprising a unit for obtaining values of the blood vessel inner diameter at a plurality of places.

8. The biological signal monitor device according to claim 7, comprising a unit for subjecting the value of the blood vessel inner diameter to angle correction based on information on a distance between a surface of an ultrasonic probe and the blood vessel wall to be observed at a plurality of places.

9. The biological signal monitor device according to claim 6, comprising a unit for comparing the amount of movement of the living tissue detected by the movement amount detection unit with a result of detecting a movement amount a predetermined number or more of cycles before, and determining a degree of stability of the measurement of the value of the blood vessel inner diameter.

10. The biological signal monitor device according to claim 6, comprising a unit for calculating a variation state of the value of the blood vessel inner diameter based on the obtained value of the blood vessel inner diameter and an amount of movement of the blood vessel wall in accordance with a heartbeat.

11. The biological signal monitor device according to claim 2, comprising, in a case where a carotid artery is to be observed, a unit for obtaining an Intima Media Thickness (IMT) value as an index of arteriosclerosis by analyzing a structure of the carotid artery based on a fact that an image in which a pulsation component due to a heartbeat is brought to a quasi-standstill and in which a random noise component is removed is obtained, or a fact that the amount of movement of the living tissue in accordance with a body motion and a vibration is detected.

12. The biological signal monitor device according to claim 11, comprising a unit for calculating IMT values at two or more places at the same time.

13. The biological signal monitor device according to claim 11, comprising a unit for displaying a region where the largest IMT value of IMT values obtained at a plurality of places is observed, on an ultrasonic image of a longitudinal cross section of a blood vessel.

14. The biological signal monitor device according to claim 11, comprising a unit for subjecting the IMT value to angle correction based on information on a distance between an ultrasonic probe and a blood vessel wall to be observed.

15. The biological signal monitor device according to claim 11, comprising a unit for comparing the amount of movement of the living tissue detected by the movement amount detection unit with a result of detecting a movement amount a predetermined number or more of cycles before, and determining a degree of stability of the measurement of the IMT value.

16. The biological signal monitor device according to claim 11, comprising a unit for comparing IMT values obtained at a plurality of places close to each other, and determining a degree of stability of the measurement of the IMT value.

17. The biological signal monitor device according to claim 11, comprising a unit for calculating a variation state of the IMT value based on the obtained IMT value and an amount of movement of a blood vessel wall in accordance with a heartbeat.

18. The biological signal monitor device according to claim 11, comprising:
  a unit for calculating a variation state of the IMT value based on the obtained IMT value and an amount of movement of a blood vessel wall in accordance with a heartbeat; and
  a unit for calculating a hardness value of an IMT measurement target region extending from a tunica intima to a tunica media based on the calculated variation amount.

* * * * *